(12) United States Patent
Wade

(10) Patent No.: US 10,620,227 B1
(45) Date of Patent: Apr. 14, 2020

(54) AUTOMATIC LIQUID SAMPLING SYSTEM AND METHOD OF USE THEREOF

(71) Applicant: Paul Wade, Bakersfield, CA (US)

(72) Inventor: Paul Wade, Bakersfield, CA (US)

(73) Assignee: PROCESS INSTRUMENTS, INC., Bakersfield, CA (US)

( * ) Notice: Subject to any disclaimer, the term of this patent is extended or adjusted under 35 U.S.C. 154(b) by 0 days.

(21) Appl. No.: 16/583,960

(22) Filed: Sep. 26, 2019

(51) Int. Cl.
| | |
|---|---|
| *G01N 35/02* | (2006.01) |
| *G01N 1/40* | (2006.01) |
| *G01N 33/28* | (2006.01) |
| *G01N 1/20* | (2006.01) |
| *G01N 35/00* | (2006.01) |

(52) U.S. Cl.
CPC ......... *G01N 35/025* (2013.01); *G01N 1/2035* (2013.01); *G01N 1/40* (2013.01); *G01N 33/2823* (2013.01); *G01N 2001/205* (2013.01); *G01N 2035/00465* (2013.01)

(58) Field of Classification Search
CPC ...... G01N 35/025; G01N 1/40; G01N 1/2035; G01N 33/23
See application file for complete search history.

(56) References Cited

U.S. PATENT DOCUMENTS

| | | | |
|---|---|---|---|
| 2,736,201 A | 2/1956 | Ohlsen et al. | |
| 4,215,567 A | 8/1980 | Vlcek | |
| 4,581,583 A * | 4/1986 | Van Vliet | G01R 33/28 324/321 |
| 4,697,462 A * | 10/1987 | Daube, Jr. | G01N 1/18 55/528 |
| 4,713,974 A * | 12/1987 | Stone | G01N 30/24 422/64 |
| 4,732,037 A * | 3/1988 | Daube, Jr. | G01N 1/18 73/170.17 |
| 5,216,926 A * | 6/1993 | Lipscomb | G01N 35/1079 73/863.01 |
| 5,553,508 A * | 9/1996 | Dabberdt | G01N 1/2273 73/863.02 |
| 6,212,948 B1 | 4/2001 | Ekdahl et al. | |
| 2002/0137194 A1 * | 9/2002 | Ammann | B01F 9/0001 435/287.1 |
| 2013/0259745 A1 | 10/2013 | Yamazaki et al. | |

FOREIGN PATENT DOCUMENTS

WO    WO2018032053 A1    2/2018

\* cited by examiner

*Primary Examiner* — John Fitzgerald
(74) *Attorney, Agent, or Firm* — James M. Duncan, Esq.; Klein DeNatale Goldner

(57) ABSTRACT

An automatic fluid sampler works in conjunction with a conventional oil well test system. The sampler utilizes a rotating platter which aligns the mouth of a sampling container with a conduit for delivery of a composite sample which is provided in incremental volumes over the duration of a well test event. Upon completion of the well test, a fresh container is rotated to be in position to receive a composite sample for a new well test event.

20 Claims, 6 Drawing Sheets

AUTOMATIC LIQUID SAMPLING SYSTEM AND METHOD OF USE THEREOF

BACKGROUND OF THE INVENTION

The present invention generally relates to devices and methods for flow measurement of fluids produced from hydrocarbon wells. More particularly, embodiments of the present invention provide an apparatus and method for obtaining a composite sample from a well in a production test mode, where the composite sample is obtained incrementally over the duration of the production test. Having the composite sample allows a precise determination of the water cut through conventional volumetric measurement methods. Once a precise water cut is determined, an oil producer can determine an accurate net oil production rate for a well. Among other uses, the observed water cut information may be utilized to accurately determine the economic limit of the well, to evaluate the success of a well treatment program, and/or to program various devices which require input of water cut information.

The water cut measurement—the percentage of water in a liquid production stream—is the most important factor in accurately determining the volume of net oil produced by an oil well. Determination of the water cut may be accomplished in a variety of ways. Some production facilities utilize three-phase flow separation systems which first separate the gas phase from the liquid phase, and then separate the liquid phase into an oil phase and a water phase and meter each liquid stream. More typically, because of the expense of three-phase flow separation systems and the retention time which may be required to sufficiently separate the oil phase from the water phase, two-phase systems are more commonly utilized. With these systems, the gas phase is separated from the liquid phase but there is no separation of the oil and water in the liquid phase. The liquid phase must then be analyzed either manually or with analytical devices to determine the water cut.

Water cut meters are the typical analytical devices utilized to determine water cut. These devices measure a liquid phase flow and then ascertain the relative percentage of water in the flow stream utilizing a variety of technologies, such as dielectric measurement (capacitance), microwave, infrared. However, utilizing water cut meters to determine net oil becomes more uncertain as the water cut increases. As the water cut in the liquid stream increases, the net oil measurement of the known water cut meters loses accuracy. In such cases, obtaining a reliable water cut measurement requires sampling the flow stream and directly measuring the percentage of water in the sample. However, such sampling is typically done by opening a valve for a brief period of time and "grabbing" a sample. However, because of changing flow conditions and flow regimes, a grabbed sample does not necessarily provide a liquid sample which is representative of the well's production over time.

Because net oil production is determined from the water cut, accurate determination of the water cut is an important factor in determining the economic viability of a well or field. Unfortunately, at the time when this information is perhaps needed the most, the accuracy of water cut data is likely to be the most difficult to achieve because an increase in water cut is common for mature, depleting water drive reservoirs. An apparatus which results in the well test systems providing accurate water cut measurement, particularly where the production stream has a high water cut, is desirable.

SUMMARY OF THE INVENTION

Embodiments of the present invention provide composite production samples which are representative of a well's production over an entire well test period, rather than a sample taken over a brief interval. Once obtained, these samples may be used to determine a well's water cut over the duration of the well test period.

Embodiments of the invention are utilized in conjunction with conventional oil well test systems. These systems generally comprise a fluid separation vessel, a flow meter and a well test controller which may, among other things, be programmed to select a particular well for testing and the length of the test. The well test controller is configured, in conjunction with various flow control valves, to route fluid flow from an oil well to the fluid separation vessel. The fluid separation vessel separates the fluid into a gas phase and a liquid phase. The gas phase may be routed to additional processing equipment, into a gas production line, or to a flare. The liquid phase will flow through the flow meter to determine the gross fluid production.

A portion of the liquid phase is directed into embodiments of the present invention. Embodiments of the invention comprise a platter connected to a motor, wherein the motor is configured to rotate the platter a fixed angular displacement upon the motor's receipt of an electrical current, wherein the platter stops rotating when the current flow to the motor is stopped. A container disposed on the platter is aligned with a conduit which delivers a liquid sample to the container. The sample may be provided to the container in incremental amounts over the entire test period by operation of a valve which controls liquid flow through the conduit. A controller opens and closes the valve to allow for the delivery of each incremental amount. The incremental amount will typically be 1.0 to 1.5 milliliters.

The controller also activates a switch which provides electrical current to the motor, so that upon the conclusion of a well test the motor is energized and advances a new container to the conduit for the start of a new well test. Once the composite liquid sample is obtained, it may be analyzed to precisely ascertain the relative percentages of water and oil.

Embodiments of the apparatus may comprise a plurality of containers, such as four, six, eight, ten and twelve containers. In one embodiment, the apparatus comprises six containers, wherein the containers are funnel-shaped with an open mouth, having a closing device, such as a valve or cap, at the end opposite the open mouth. The containers may have a volume ranging from 500 to 2000 milliliters. For an apparatus comprising six containers, the fixed angular displacement will be 60 degrees. The containers may be set within a plurality of radially adjacent openings in the platter, with a single container disposed within each opening. A position switch may be utilized to ascertain the position of each container.

Embodiments of the apparatus may be utilized in a method of obtaining a composite sample from an oil well during a well test. In this method, a flow of fluid from an oil well is directed to a test separator, where the test separator separates the fluid flow delivered into the test separator into a liquid phase and a gas phase. A portion of the liquid phase is directed through a flow meter to a conduit which is connected to the automatic liquid sampling system as described above. The automatic liquid sampling system is utilized to obtain a composite liquid sample which is taken in increments over the period of the entire well test. Once the composite liquid sample is obtained, it may be analyzed, such as by separation of the water phase and the oil phase by gravity, centrifuge, and/or chemical treatment, such as emulsion breakers.

DETAILED DESCRIPTION OF THE INVENTION

Figure 1:
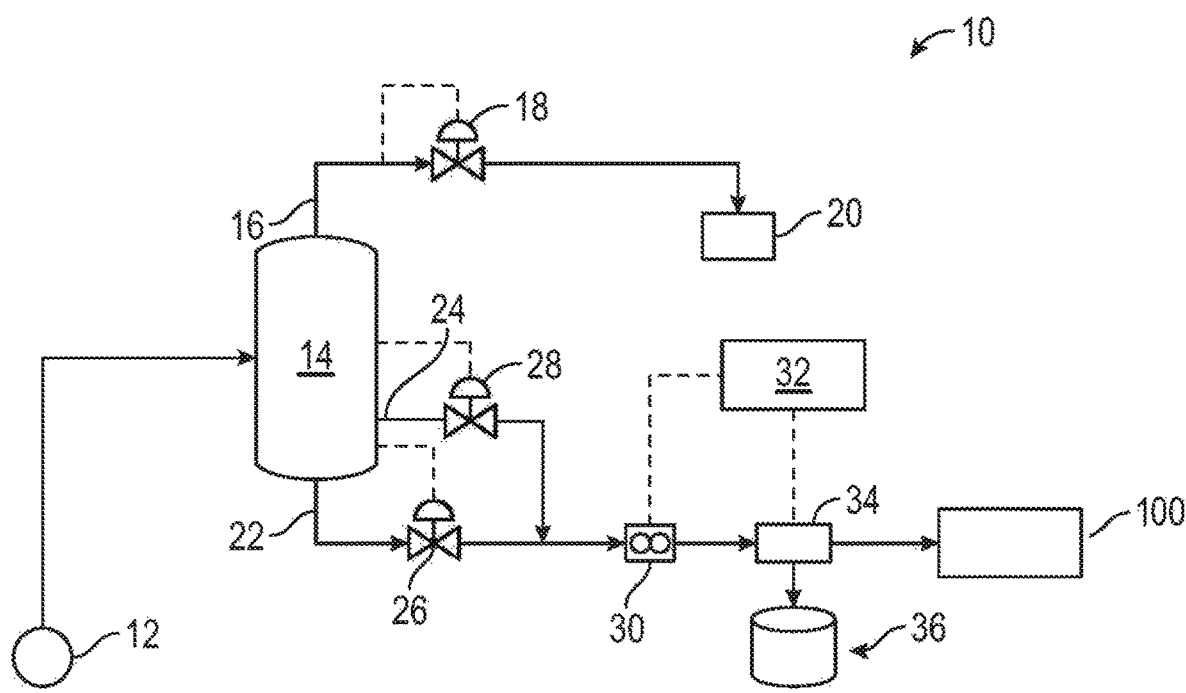
FIG. 1 schematically depicts an oil well flowing into an oil well test system equipped with an embodiment of the invention.

Referring now to the Figures, FIG. 1 schematically depicts an oil well test system 10 for testing an oil well 12. Fluids from oil well, typically comprising gas, oil and water, flow into a test separation vessel 14. Test separation vessel 14 allows gas phase to flow out through gas outlet 16 as controlled by control valve 18 and into a gas processing system 20 for further processing and disposition. The liquid phase, comprising an oil phase and a water phase, is typically separated by gravity. The water phase will flow out through the bottom of the test separation vessel 14 through bottom outlet 22 and the oil phase will flow out through an intermediate portion of the test separation vessel 14 through intermediate outlet 24. Flow out of the bottom outlet is controlled by control valve 26 and flow out of the intermediate outlet 24 is controlled by control valve 28. Flow of the combined oil phase and water phase go through flow meter 30, which may provide output to controller 32. Controller 32 will also control well selection for the well test and the duration of the well test. Controller 32 may also have a totalizer which records flow through flow meter 30.

Flow meter 30 may be a full range water cut meter. If it is determined, whether by controller 32 or by manual input that the accuracy of flow meter 30 is questionable or needs to be proven up, liquid sampling controller 34 will divert at least a portion of the flow from test separation vessel 14 to automatic sampling unit 36, where the flow is provided in a series of incremental samples which are provided over the entire test period for the well 12. The remainder of the flow is returned to the production system 100. The incremental samples will generally be 1.0 to 1.5 cubic centimeters per each sampling event.

Figure 2:
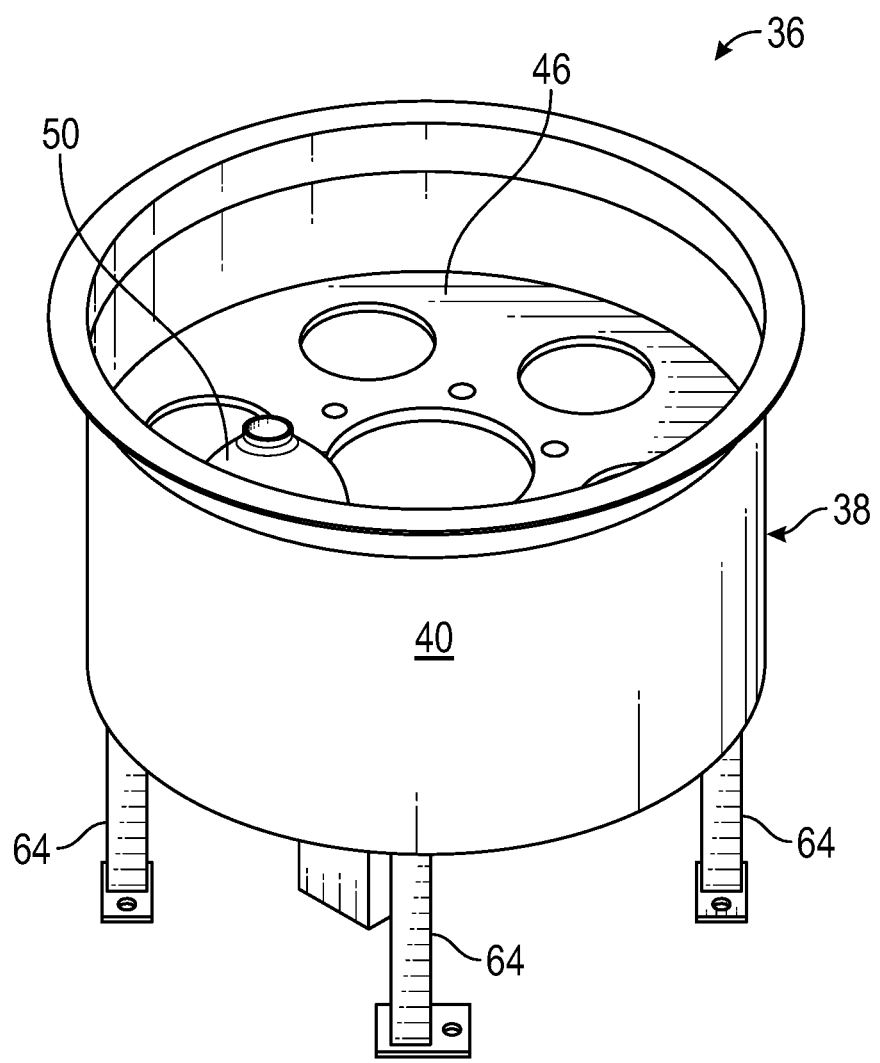
FIG. 2 is a perspective view of an embodiment of the automatic sampling unit of the present invention.
Figure 3:
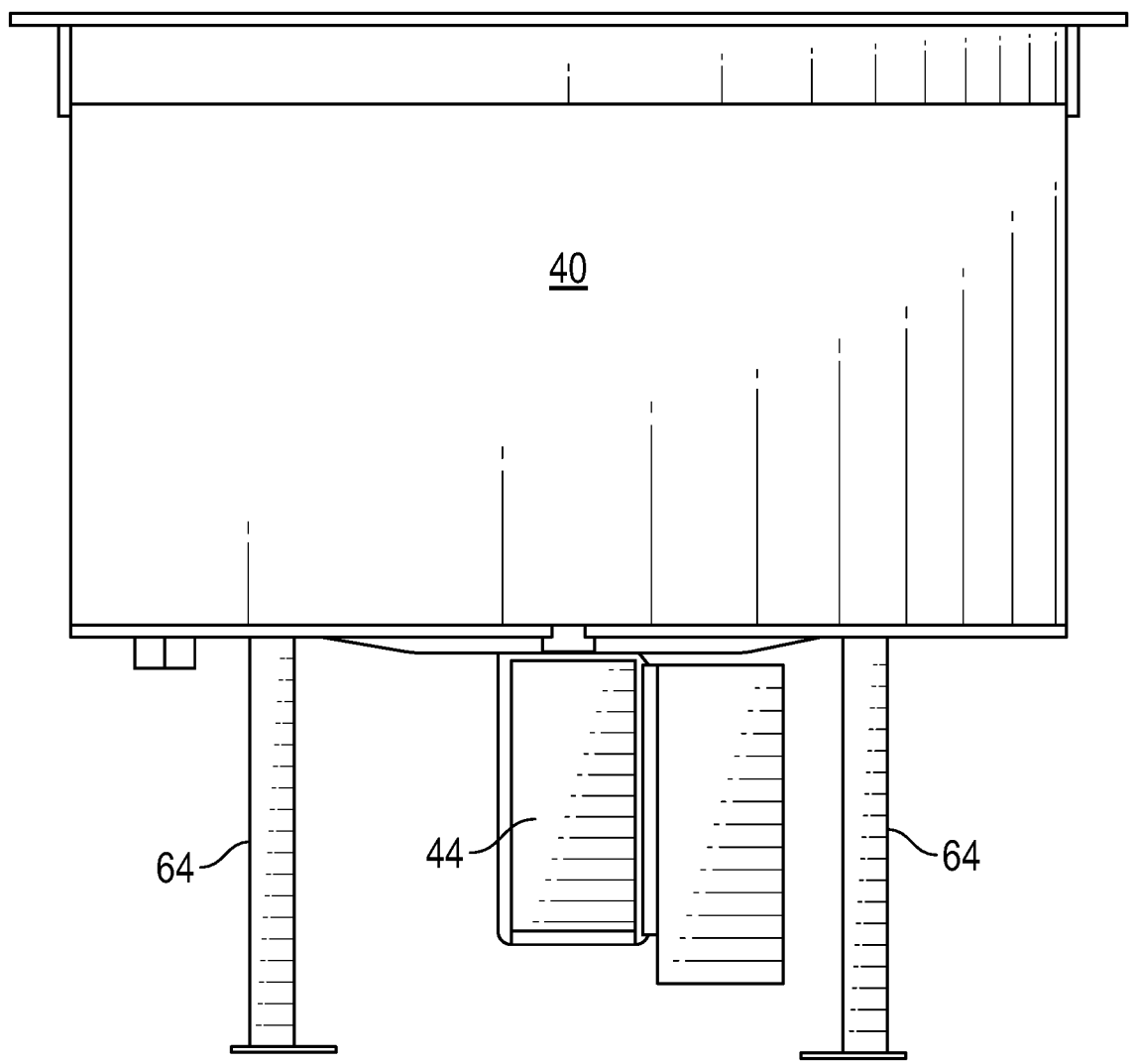
FIG. 3 is an elevational view of the embodiment of the automatic sampling unit depicted in FIG. 2.
Figure 4:
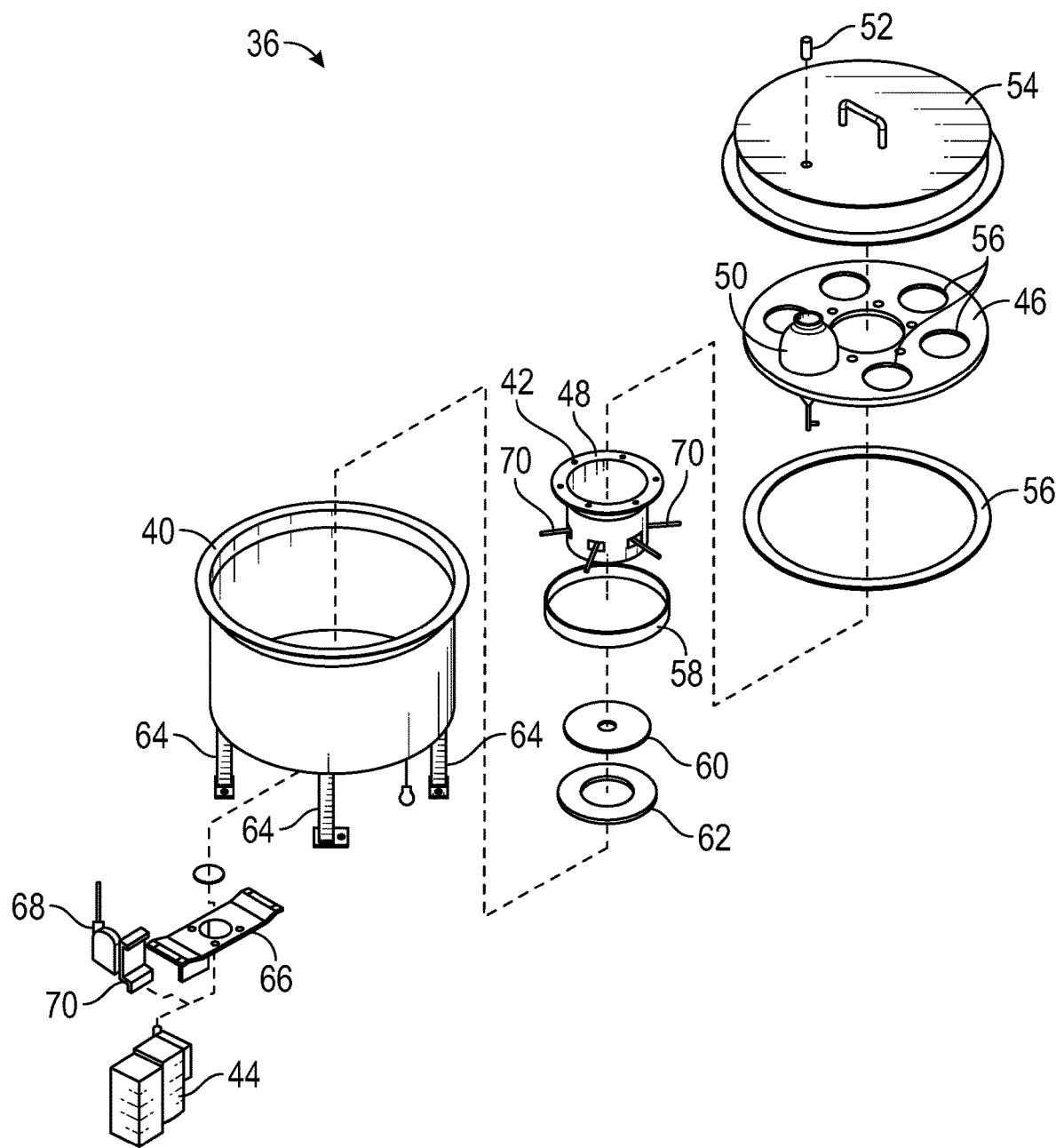
FIG. 4 is an exploded view of the automatic sampling unit of FIG. 2.
Figure 5:
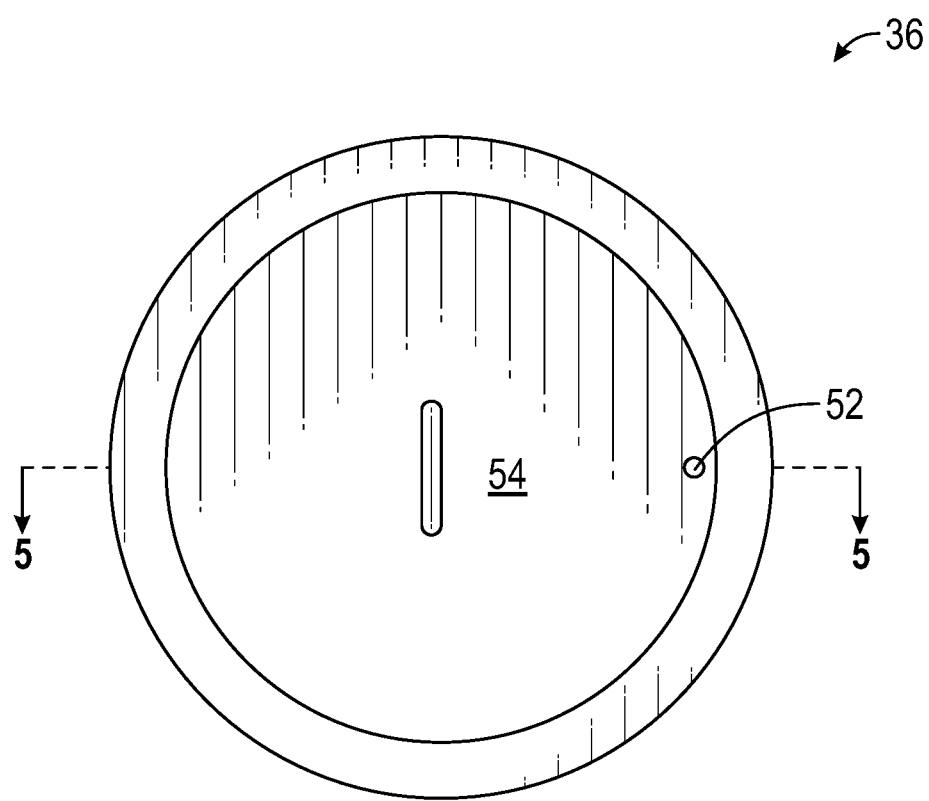
FIG. 5 is a top view of an embodiment of an automatic sampling unit.
Figure 6:
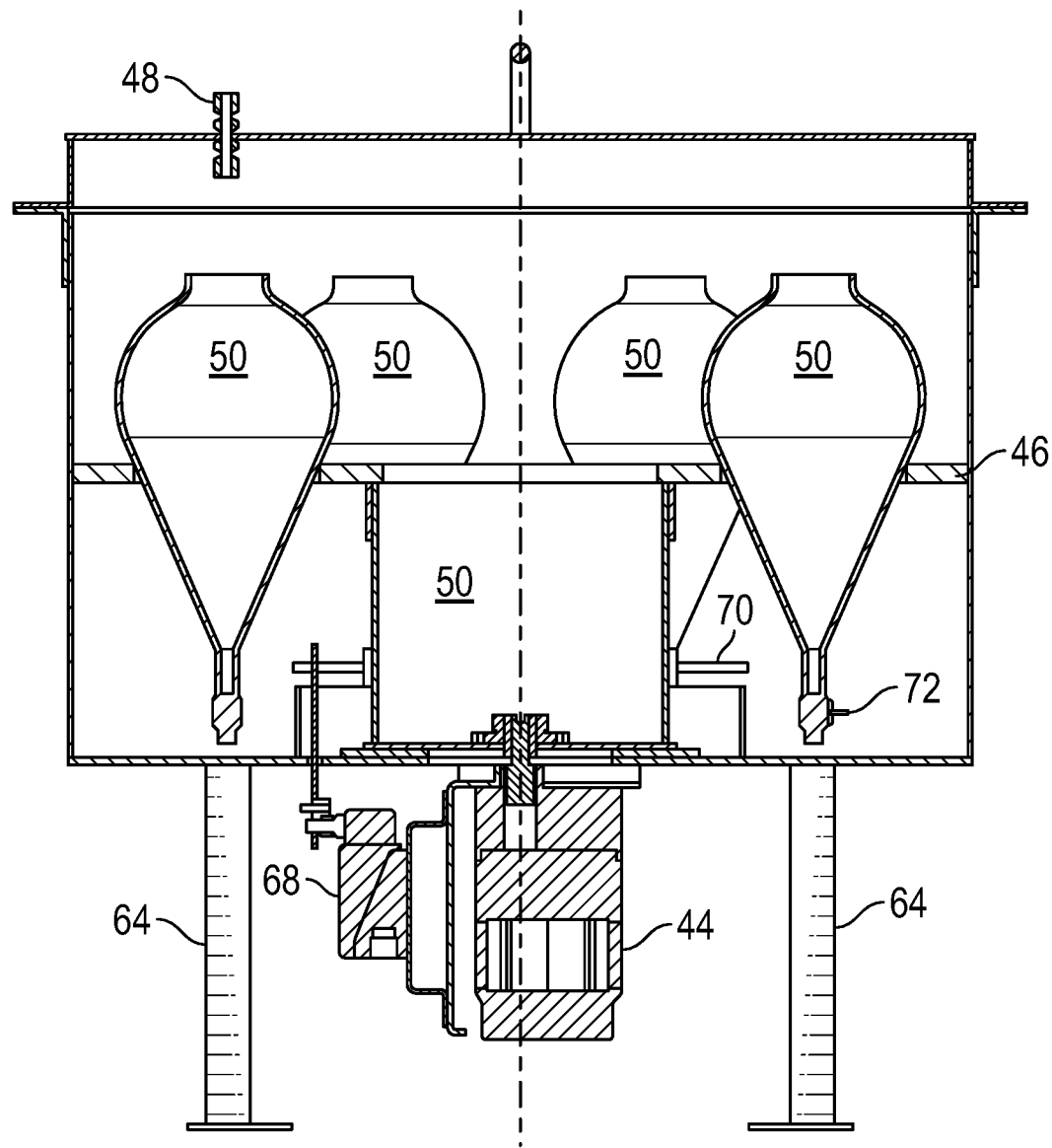
FIG. 6 is a sectional view taken along line 5-5 of the automatic sampling unit of FIG. 5.

FIG. 2 depicts an embodiment of the automatic sampling unit 36. The automatic sampling unit 36 comprises a carousel unit 38. As best shown in FIG. 4, carousel unit 38 has a housing 40, an inner cylinder 42 disposed within the housing and a motor 44 which is configured to rotate the inner cylinder. The motor 44 is configured to rotate the inner cylinder 42 a fixed angular displacement upon receipt of an electrical current which is provided by a switch activated and deactivated by liquid sampling controller 34. The carousel unit 38 also has a platter 46 which is attached to an upward facing surface 48 of inner cylinder 42.

An open mouth container 50 is contained within the carousel unit 38. A fluid inlet 52 delivers the series of incremental samples to the open mouth container 50. The desired fill volume of open mouth container 50 may be inputted into liquid sampling controller 34 and the volume of each incremental sample may be also programmed such that liquid sampling controller 34 may determine when the open mouth container is approaching the desire fill volume. The incremental sample size and sampling frequency may be programmed such that the open mouth container 50 is nearly full at the conclusion of the well test event. Liquid sampling controller 34 may interact with controller 32 and/or with flow meter 30 to determine the rate of sample for the duration of the test. Liquid sampling controller may also interact with controller 32 to coordinate various parameters such as the well test schedules, the well test lengths, and sample volume for each well test. When a well test is concluded, inner cylinder 42 and platter 46 are rotated by motor 44 so that a new open mouth container 50 is aligned with fluid inlet 52 for the start of a new well test event.

In one embodiment of the invention, motor 44 starts and stops every sixty degrees. In this embodiment, platter 46 may comprise six dedicated openings 56, with an open mouth container set within each opening. A cover unit 54 may be utilized to cover each of the open mouth containers 50. Fluid inlet 52 may be set within the cover unit 54, such that an opening at the top of open mouth container aligns with the fluid inlet upon each activation of motor 44. Other components of carousel unit 38 may include support ring 56, splash guard 58, bushing 60, and drip pan 62. Housing 40 may be supported by legs 64.

Motor 44 may be mounted to the automatic sampling unit 36 with mount 66. Limit switch 68 may be mounted to mount 70. Limit switch 68 may be activated by limit switch contacts 66 on inner cylinder 42.

Containers 50 may be in a funnel configuration with a sealed bottom end. However, a valve 72 may be placed at the bottom of the container 50 to allow draining of the container.

Each composite sample is analyzed manually to ascertain an accurate water cut. The sample may also be analyzed for fluid chemistry and fluid properties. Data acquired from the analysis may be uploaded into the well analysis system for calibration of water cut meters and other automated analysis devices.

Having thus described the preferred embodiment of the invention, what is claimed as new and desired to be protected by Letters Patent includes the following:

1. An automatic liquid sampling system utilized in conjunction with an oil well test system, the oil well test system of the type comprising a fluid separation vessel, a flow meter, and a well test controller, the well test controller configured to route a fluid flow from an oil well to the fluid separation vessel, wherein the fluid separation vessel separates the fluid flow into a liquid phase and a gas phase, the automatic liquid sampling system comprising:
   a carousel unit, the carousel unit comprising a housing, an inner cylinder disposed within the housing, a platter attached to an upward facing surface of the inner cylinder, and a motor configured to rotate the inner cylinder a fixed angular displacement upon receipt of an electrical current, wherein the platter comprises a plurality of open mouth containers;
   a conduit connected to the fluid separation vessel, wherein the conduit delivers a portion of the liquid phase into an open mouth container of the plurality of open mouth containers upon alignment of the open mouth container with the conduit; and
   a controller which activates a switch to provide the electrical current to the motor.

2. The automatic liquid sampling system of claim 1 wherein the platter comprises a plurality of radially adjacent openings, wherein an open mouth container of the plurality of open mouth containers is disposed within each of the plurality of radially adjacent openings.

3. The automatic liquid sampling system of claim 2 wherein each of the plurality of open mouth containers comprises a funnel having a bottom end with a valve which seals the bottom end.

4. The automatic liquid sampling system of claim 1 wherein the plurality of open mouth containers comprises a total of six open mouth containers.

5. The automatic liquid sampling system of claim 4 wherein each of the open mouth containers of the plurality of open mouth containers is equally spaced on the platter.

6. The automatic liquid sampling system of claim 5 wherein the fixed angular displacement is 60 degrees.

7. The automatic liquid sampling system of claim 1 wherein the portion of the liquid phase delivered into the open mouth container is delivered in a plurality of increments spaced over a period of time of a well test to provide a composite liquid sample for the well test.

8. The automatic liquid sampling system of claim 7 wherein a programmable controller provides a signal to an automated valve to open and close over the period of time of the well test to provide the composite liquid sample through the conduit.

9. The automatic liquid sampling system of claim 8 wherein each increment ranges from 1.0 to 1.5 milliliters.

10. The automatic liquid sampling system of claim 9 wherein each container of the plurality of containers has a storage volume ranging from 500 to 2000 milliliters.

11. The automatic liquid sampling system of claim 10 wherein the programmable controller receives a signal from a flow meter and determines a total volume of the portion of the liquid phase delivered into the open mouth container.

12. The automatic liquid sampling system of claim 11 wherein the programmable controller tracks the volume of the increments delivered to the container and instructs the well test controller to stop the well test when the volume of the increments is equivalent to the container volume.

13. The automatic liquid sampling system of claim 12 further comprising a position switch which senses the position of each of the plurality of open mouth containers.

14. The automatic liquid sampling system of claim 13 wherein at the conclusion of a first well test the programmable controller causes a next radially adjacent open mouth container to be placed in a position to be filled by the conduit over the course of a second well test.

15. A method of obtaining a composite sample from an oil well during a well test comprising the steps of:
directing a flow of fluid from an oil well to a test separator over a well test period, wherein the test separator separates the fluid flow delivered into the test separator into a liquid phase and a gas phase;
directing a portion of the liquid phase through a flow meter to a conduit connected to an automatic liquid sampling system, the automatic liquid sampling system comprising a plurality of open mouth containers, the automatic liquid sampling system further comprising a motor which positions a single open mouth container of the plurality of open mouth containers to receive the portion of the liquid phase in a plurality of increments over the well test period to provide a composite liquid sample into the single open mouth container; and
analyzing the composite liquid sample to ascertain a percentage of total water contained in the composite liquid sample.

16. The method of claim 15 wherein the automatic liquid sampling system comprises a carousel unit, the carousel unit comprising a platter comprising the plurality of open mouth containers and the motor is configured to rotate the platter.

17. The method of claim 15 wherein each of the plurality of open mouth containers comprises a funnel having a bottom end with a valve which seals the bottom end.

18. An automatic liquid sampling system utilized in conjunction with an oil well test unit, the oil well test unit of the type comprising a fluid separation vessel, a flow meter, and a well test controller, the well test controller configured to route a fluid flow from an oil well to the fluid separation vessel, wherein the fluid separation vessel separates the fluid flow into a liquid phase and a gas phase, the automatic liquid sampling system comprising:
a conduit which receives a portion of the liquid phase;
a platter connected to a motor, the motor configured to rotate the platter a fixed angular displacement upon receipt of an electrical current;
a plurality of open mouth containers disposed upon the platter, wherein an open mouth container is positioned beneath the conduit when the platter is rotated the fixed angular displacement; and
a controller which activates a switch to provide the electrical current to the motor.

19. The automatic liquid sampling system of claim 18 wherein the portion of the liquid phase is delivered through the conduit into the open mouth container in a plurality of increments spaced over a period of time of a well test to provide a composite liquid sample for the well test.

20. The automatic liquid sampling system of claim 19 wherein a programmable controller provides a signal to an automated valve to open and close over the period of time of the well test to provide the composite liquid sample through the conduit into the open mouth container.

* * * * *